United States Patent [19]

Cech

[11] 4,364,388
[45] Dec. 21, 1982

[54] SYRINGE DISPENSING APPARATUS

[76] Inventor: Jerry E. Cech, 4383 E. Mt. Morris Rd., Mt. Morris, Mich. 48458

[21] Appl. No.: 255,197

[22] Filed: Apr. 20, 1981

[51] Int. Cl.$^3$ .............................................. A61M 1/00
[52] U.S. Cl. ................................ 128/234; 128/218 C
[58] Field of Search ............... 128/213 R, 215, 218 R, 128/218 C, 234, 236

[56] References Cited

U.S. PATENT DOCUMENTS

| | | | |
|---|---|---|---|
| 2,523,850 | 9/1950 | Steinberg | 128/218 C |
| 3,110,310 | 11/1963 | Cislak | 128/218 C |
| 3,695,266 | 10/1972 | Lussier | 128/218 C |
| 3,835,835 | 9/1974 | Thompson et al. | 128/218 C |
| 4,022,207 | 5/1977 | Citrin | 128/218 C |

*Primary Examiner*—John D. Yasko
*Attorney, Agent, or Firm*—Cullen, Sloman, Cantor, Grauer, Scott & Rutherford

[57] ABSTRACT

The syringe dispensing apparatus of this invention is adapted to dispense fluid under pressure from or vacuum fill a conventional plastic disposable syringe having a cylindrical reservoir and a piston plunger having an elongated body portion, generally cruciform in cross-section with radially extending vanes. The dispensing apparatus includes a hand operated ratchet mechanism and a supporting alignment collar which is received around the syringe reservoir, at the open end. The collar has a transverse flange including a slot which receives one of the vanes of the plunger, which aligns the ratchet mechanism on the syringe. The ratchet mechanism includes a pair of handles releasably attached to the opposed ends of the collar and a sharp detent which digs into and grips one of the opposed aligned vanes of the plunger, to telescope the plunger into the syringe reservoir and dispense a metered volume of fluid through the restricted syringe outlet.

9 Claims, 4 Drawing Figures

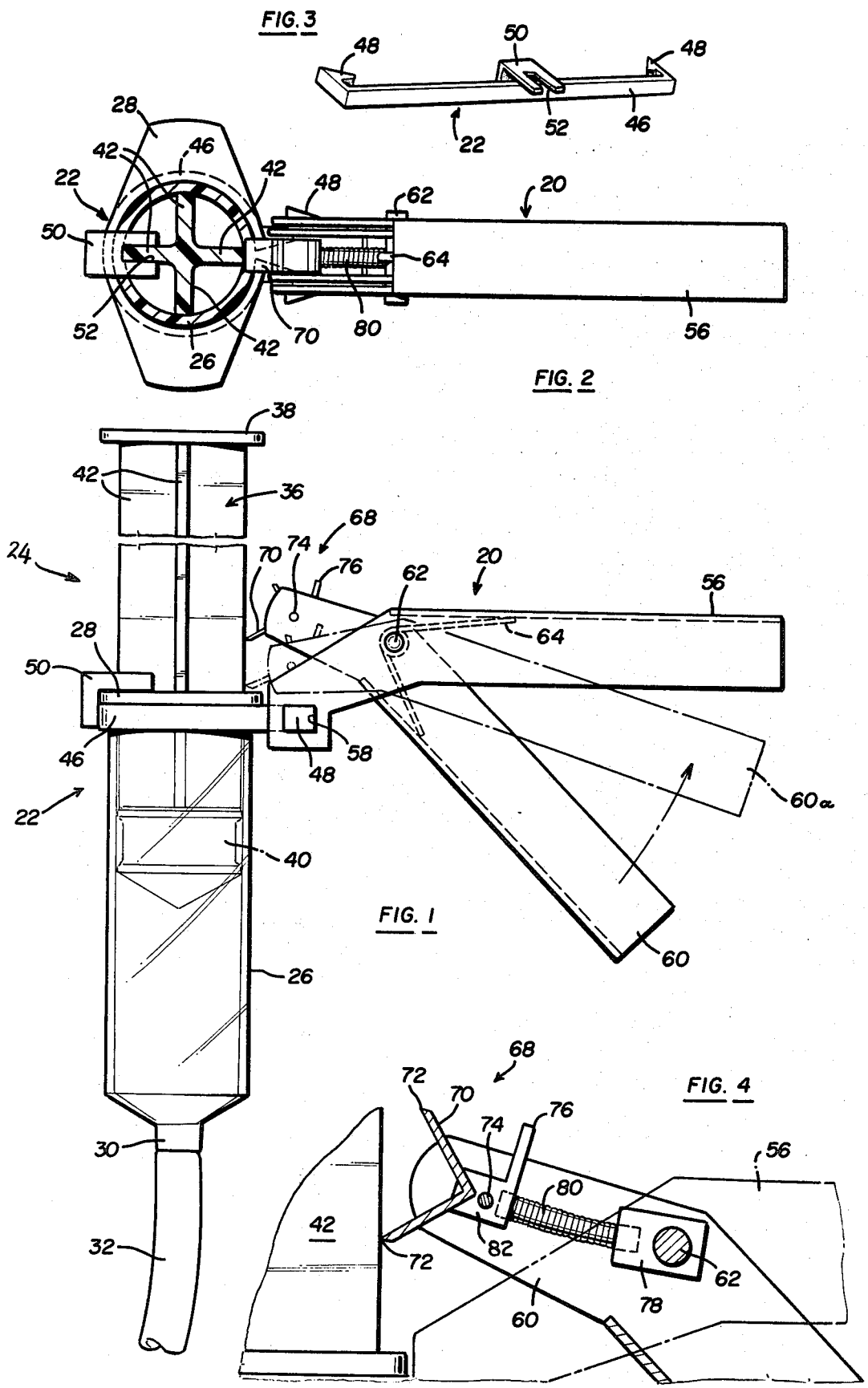

SYRINGE DISPENSING APPARATUS

FIELD OF THE INVENTION

The present invention relates to a dispensing apparatus for a syringe or hypodermic having a plunger or piston. The dispensing device of this invention utilizes a spring actuated ratchet mechanism.

The prior art includes a number of syringe and hypodermic dispensing devices and apparatus, including devices wherein the piston or plunger is operated by a ratchet mechanism for dispensing metered quantities of fluid under pressure. In the prior art, the ratchet-dispensing device is generally integral with the syringe or hypodermic, wherein the plunger includes ratchet slots which are engaged and operated by the ratchet mechanism of the dispensing device. The syringe is thus intended to be reused, requiring cleaning, sterilizing, etc. The following United States Patents illustrate this type of syringe dispensing apparatus: U.S. Pat. Nos. 530,187, 780,147, 1,751,139, 2,316,095, 3,160,156 and 3,504,673. U.S. Pat. No. 2,892,457 discloses a hypodermic syringe dispensing device wherein the ratchet mechanism is separate from the syringe, however the dispensing mechanism is quite complex and limited by the type and size of hypodermic syringe. The mechanism is not adapted for use with a conventional disposable plastic syringe.

The most common syringe presently used for medical applications is a disposable plastic syringe comprising a cylindrical reservoir or barrel and a plunger-piston, which is telescopically received in the reservoir. The elongated plunger is cruciform in cross-section, having four radially extending vanes. A resilient cylindrical piston is snapped onto the end of the plunger for dispensing fluid from the restricted opening in the fluid reservoir as the piston is forced into the reservoir under hand pressure. Disposable plastic syringes vary in volume from 0.5 to 10 cubic centimeters to 50 cc and greater. The larger volume syringes are very difficult to administer by hand and nearly impossible to self administer. For example, in chemotherapy and in performing an amniocentesis, 30 cc or more fluid may be administered into or out of a disposable syringe.

The prior art does not however disclose a simple dispensing apparatus suitable for disposable plastic syringes, particularly the large volume syringes that are very difficult to self administer. A principal object of the present invention is to provide a simple dispensing device for disposable plastic syringes.

SUMMARY OF THE INVENTION

As described, the dispensing apparatus of this invention is particularly adapted to dispense metered volumes of fluid from or vacuum fill a conventional plastic syringe, such as the disposable syringes commonly used in medical and veterinary applications. The conventional syringe includes a tubular cylindrical fluid reservoir or barrel portion having an open end and terminating in a restricted dispensing outlet. A plunger is telescopically received within the tubular reservoir open end for dispensing fluids through the restricted outlet. In the conventional disposable plastic syringe, the plunger is cruciform in cross-section having four radially extending vanes and a resilient cylindrical piston is snapped onto the end of the plunger. The plunger is pressed into the reservoir to force fluid out of the reservoir outlet.

The dispensing apparatus of this invention includes an alignment-retainer collar having an elongated strap portion, which is receivable around the cylindrical syringe reservoir adjacent the open end. A hand operated ratchet mechanism attaches to the collar and engages the plunger to telescope the plunger into the reservoir. The ratchet mechanism includes a fixed handle which is releasably attached to the opposed ends of the collar strap portion and a spring biased movable handle which is pivotally attached to the fixed handle, spaced from its opposed ends, providing a scissors-like movement. A spring biased detent having a sharp edge is pivotally attached on the free end of the movable handle, opposite the syringe plunger, such that the detent cuts and releasably grips the plunger upon pivotal movement of the movable handle, telescoping the plunger into the reservoir and dispensing fluids from the syringe.

In the preferred embodiment of the syringe dispensing apparatus of this invention, the collar includes an alignment means which aligns the collar and the attached ratchet mechanism relative to the vanes of the plunger, such that the detent is operatively aligned with a plunger vane. In the disclosed embodiment, the mid-portion of the collar includes a transverse birfurcated flange having a slot which receives one of the vanes of the plunger. The collar is thus aligned on the cylindrical reservoir relative to the plunger vanes. The ratchet mechanism, which is attached to the free ends of the collar strap, is thus aligned on the plunger, opposite the collar flange. The detent is thus operably aligned to engage one of the plunger vanes to operate the plunger.

The ratchet detent in the preferred embodiment of the invention is generally V-shaped having sharp edges to dig into and grip the aligned plunger vane. The detent is pivotally supported on the free end of the movable handle, opposite the plunger. In the disclosed embodiment, the detent includes a release lever to rotate one or the other of the detent legs into biting engagement with the aligned plunger vane. The plunger may thus be operated to telescope into or out of the tubular reservoir for dispensing fluids or filling the reservoir by squeezing and releasing the spring biased handle, depending upon the position of the release lever.

The syringe dispensing device of this invention is attached to a conventional plastic syringe by locating the alignment means on a plunger vane and wrapping the collar around the cylindrical reservoir, adjacent the plunger. A conventional disposable syringe includes a flange portion which is normally gripped by the first and second fingers, and the plunger is moved by the thumb. The collar is preferably received around the reservoir, beneath the flanges. The ratchet mechanism is then attached to the free ends of the collar and the dispensing mechanism is ready for operation. In the disclosed embodiment, the free ends of the collar strap include enlarged tabs which are snapped into and retained in slots in the stationary handle, retaining the handle on the syringe reservoir and aligning the ratchet detent with a radially extending vane of the plunger.

The syringe dispensing apparatus of this invention is thus relatively simple in construction and easy to attach to and operate a conventional disposable plastic syringe. Other advantages and meritorious features of the present invention will be more fully understood from the following description of the preferred embodiments, the appended claims and the drawings, a brief description of which follows.

BRIEF DESCRIPTION OF THE DRAWINGS

FIG. 1 is a side elevation of one embodiment of the dispensing apparatus of this invention operating a conventional disposable plastic syringe;

FIG. 2 is a top elevation of the embodiment of the dispensing apparatus shown in FIG. 1 with the plunger in cross-section;

FIG. 3 is a top elevation of the collar of the dispensing apparatus shown in FIGS. 1 and 2 in the relaxed extended position; and FIG. 4 is an enlarged view of the ratchet detent shown in FIG. 1 in the operating position, with the handles in phantom for illustration.

DESCRIPTION OF THE PREFERRED EMBODIMENTS

The disclosed embodiment of the syringe dispensing apparatus of this invention includes a ratchet mechanism 20 and a collar 22 which aligns and attaches the ratchet mechanism to the syringe 24 for operation of the syringe. As described above, the dispensing apparatus of this invention is particularly adapted to operating a conventional disposable plastic syringe which includes a reservoir or barrel portion 26 and a plunger 36. The reservoir or barrel portion 26 is generally cylindrical, including an integral radially extending flange portion 28 and a restricted fluid outlet 30. A plastic flexible tube or hose 32 may be attached to the outlet of the syringe, particularly larger volume syringes. A hypodermic needle, not shown, is attached to the end of the hose. Alternatively, a hypodermic needle may be attached to the syringe outlet, particularly with the smaller volume syringes.

The plunger 36 includes an integral transverse top member 38 and a resilient cylindrical piston 40, which is normally a separate member snapped onto the end of the plunger. In a typical disposable plastic syringe, the end of the plunger includes integral spaced circular transverse discs on a pointed web and the resilient piston is snapped over the end disc, securely retaining the piston on the plunger. As best shown in FIG. 2, the plunger 36 is cruciform in cross-section, including four radially extending vanes 42, thereby reducing the weight and the material requirements of the plunger, without sacrificing strength.

The syringe is normally operated by hand by filling the reservoir 26 with the fluid to be dispensed and telescoping the plunger into the reservoir. Preloaded syringes are also commercially available. The plunger is depressed by gripping the opposed flanges 28 beneath the first and second fingers and depressing the plunger by pressing the thumb against the top member 38. The hand operation of the syringe may be very difficult for a person with small hands, particularly the larger syringes having a volume of 35 cc or greater. The operation is particularly difficult for self administrating large doses of fluids. The operating mechanism of the present invention eliminates this problem by providing a convenient hand ratchet mechanism, as now described.

The ratchet mechanism 20 is attached to the reservoir or barrel portion 26 of the syringe in the disclosed embodiment by a collar 22. As best shown in FIG. 3, the collar includes an elongated strap portion 46, which terminats at its distal ends in generally C-shape locking tabs 48. An integral generally L-shaped flange 50 projects upwardly and then transversely from the midportion of the strap. A slot 52 is provided in the laterally extending portion of the flange, which receives a radially extending vane 42 of the plunger, as shown in FIGS. 1 and 2 and described hereinbelow.

The ratchet mechanism 20 includes a stationary or fixed handle member 56, which is generally U-shaped in cross-section and includes rectangular slots 50 at one end, as best shown in FIG. 1. The C-shaped tabs 48 of the collar are snapped into the slots 58, as shown in FIG. 1, to retain the fixed handle on the collar. A movable handle member 60 is pivotally attached to the fixed handle 56 intermediate its ends by rivot 62. The movable handle is spring biased by the L-shaped spring member 64 which includes a center portion wound around the rivot and opposed ends which are spring biased against the fixed and movable handles, 56 and 60, respectively. As best shown in FIGS. 1 and 2, the movable handle 60 nests within the fixed handle 56, with the rivot 62 providing a scissors-like motion.

The ratchet means 68 is best shown in FIG. 4. The ratchet means includes a generally V-shaped detent 70 having sharp edges 72 adapted to dig into and grip the vane 42 of the plunger, as described hereinbelow. The detent is pivotally supported on the free end of the movable handle 60 by rivot 74 and the detent includes an integral release lever 76 for rotating the V-shaped detent, as described below. The detent is spring biased by coil spring member 80, which is compressed between the detent 70 and pivot block 78. One end of the coil spring 80 is received in a cylindrical aperture in the pivot block 78 and the pivot block is rotatably supported on rivot 62. The opposed end of the spring 80 is received in a cylindrical aperture in detent 70, thereby spring biasing the cutting edge 72 of the detent into the plunger vane 42, as described below. The detent, including the V-shaped detent 70 and the lever 76 may be integral, or a V-shaped groove may be provided in a pivot block 82 which receives and retains the V-shaped detent 70.

The plunger 36 and the reservoir or barrel portion 26 of a conventional disposable syringe are formed of an inexpensive easily formable plastic, such as polyvinyl acetate or polyethylene. The resilient piston 40 is formed of a softer material, such as polyurethane, which will form a seal with the cylindrical internal wall of the reservoir 26. The collar 22 of the dispensing apparatus of this invention may also be inexpensively formed of polyethylene or a similar plastic material, and thus disposable. The handles 56 and 60 may be stamped metal parts of steel or aluminum. The spring 80 may be a cylindrical coil spring. The V-shaped detent 70 is preferably formed of spring steel or surgical steel to hold sharp cutting edges 72. The edges 72 thus easily dig into and grip the aligned plastic vane 42 of the plunger 24 to telescope the plunger into or out of the reservoir portion 26 of the syringe.

The ratchet mechanism is attached to the barrel and aligned with the plunger of the syringe by inserting a radial vane 42 of the plunger into slot 52 of flange 50 of the collar, as shown in FIG. 2. The strap portion 46 of the collar is then wrapped around the cylindrical reservoir 26 of the syringe, beneath the radial flanges 28, as shown in FIG. 1. The C-shaped locking tabs 48 of the collar are then received between the side walls of the U-shaped fixed handle 56 and the tabs 48 are snapped into the square openings or slots 58 of the handle to secure the ratchet mechanism on the syringe as best shown in FIGS. 1 and 2. The release handle 76 is then rotated in a clockwise direction, as shown in FIGS. 1 and 4, to dig the cutting edge 72 of the lower detent into the aligned vane 42 of the plunger. As best shown in FIG. 2, the flange 50 of the collar aligns the opposed vane 42 with the detent 70 and restricts inadvertent axial movement of the plunger. The ratchet mechanism 20 is now ready for dispensing fluid from or vacuum filling the syringe 24.

The movable handle 60 is rotated by squeezing the handles together. This rotates handle 60 in a counterclockwise direction to the position shown at 60a in FIG. 1. The opposed free end of the movable handle is thus rotated in a counterclockwise direction about rivot 62 to telescope the piston 40 into the reservoir 26, dispensing fluid through the restricted opening 30 of the syringe, through tube 32. The fluid is thus dispensed under a constant pressure, which may be accurately controlled by operation of the handles. When the handle 60 is released, the spring 64 returns the handle to its operating position, as shown in FIG. 1. The movement of the piston is reversed by rotating release handle 76 in a counterclockwise direction, releasing the lower cutting edge of the V-shaped detent and engaging the upper edge for vacuum filling the syringe. Movement of handle 60 in a counterclockwise direction now reverses the movement of the piston, telescoping the piston 40 out of the reservoir and creating a vacuum in the reservoir. The C-shaped tabs are easily released by finger pressure by pushing the tabs rearwardly in FIG. 1 to release the hook-shaped ends of the tabs, releasing the ratchet mechanism.

It will be understood that various modifications may be made to the collar and ratchet mechanism of the dispensing apparatus of this invention. For example, the collar 22 may be formed from an extruded part. One end of the strap may be permanently attached to the fixed handle and a single spring biased detent may be used where reverse movement of the plunger is not required. It may also be possible to provide an attachment collar which is integral with the barrel of the syringe in certain applications. Other modifications may also be made to the disclosed embodiment of the dispensing apparatus of this invention, without departing from the perview of the appended claims, which follow.

I claim:

1. A metering dispensing apparatus for a conventional plastic syringe, said syringe having a tubular cylindrical fluid reservoir having an open end and termination in a restricted dispensing outlet, said syringe having a reciprocal plunger including a resilient cylindrical piston telescopically received in said reservoir through said open end for dispensing fluids through said restricted reservoir outlet, said plunger having an elongated radially projecting portion, said dispensing apparatus comprising a retainer collar having an elongated flexible strap portion receivable around said syringe reservoir adjacent said open end and a hand operated ratchet mechanism attachable to said collar, said hand ratchet mechanism including a fixed handle releasably attached to said collar strap portion, a spring biased movable handle pivotally attached to said fixed handle intermediate its ends and a spring biased ratchet means including a detent having a sharp edge pivotally supported on the free end of said movable handle adjacent said syringe plunger, and an alignment means on said strap portion aligning said radially projecting portion of said plunger with said detent, said ratchet means detent adapted to releasably grip said plunger radially projecting portion upon pivotal movement of said movable handle telescoping said plunger into said reservoir and dispensing fluids through said restricted reservoir opening.

2. The syringe dispensing apparatus defined in claim 1, characterized in that said opposed ends of said collar strap include enlarged tab portions which are releasably received in slots in said fixed handle, releasably retaining said fixed handle on said syringe reservoir.

3. The syringe dispensing apparatus defined in claim 1, characterized in that said detent is generally V-shaped and is pivotally supported on said movable handle free end, the distal ends of said V-shaped detent having sharp edges to dig into said plunger and said detent having a transverse release lever for rotating said detent about said pivotal support to release the edge in engagement with said plunger and dig the opposed edge into said plunger.

4. The syringe dispensing apparatus defined in claim 1, characterized in that said plunger has radially extending vanes, said alignment means receiving and releasably retaining one of said plunger vanes and aligning said collar relative to said plunger and said detent relative to one of the opposed vanes of said plunger for cutting and gripping said opposed plunger vane.

5. The syringe dispensing apparatus defined in claim 4, characterized in that said plunger is generally cruciform in cross-section, including four radially extending vanes, said collar alignment means comprising a bifurcated flange extending transversely from the midportion of said strap portion, said fixed handle attached to said opposed free ends of said strap, generally opposite said bifurcated flange alignment means, said flange thereby aligning said detent with the opposed plunger vane for gripping engagement.

6. The dispensing apparatus for a conventional plastic syringe, said syringe including a cylindrical fluid reservoir having an open end portion and a restricted outlet, a plunger telescopically received in said reservoir, through said open end having a resilient cylindrical piston end portion and an elongated body portion, said plunger body portion having a plurality of radial vanes, said dispensing apparatus comprising a collar including an elongated resilient strap portion receivable around said cylindrical reservoir portion, adjacent said open end, and said collar having an alignment means releasably attachable to one of said plunger body portion vanes aligning said collar relative to said plunger vanes, and a hand operated ratchet means, said ratchet means including a fixed handle releasably attached to the opposed ends of said collar strap portion, a movable handle pivotally attached to said fixed handle intermediate its ends and a spring biased ratchet means, said ratchet means including a detent pivotally supported on the free end of said movable handle opposite said syringe plunger, said detent aligned with one of said plunger body vanes by said collar alignment means, said detent having a sharp edge adapted to dig into said one vane upon pivotal movement of said movable handle, telescoping said plunger into said reservoir and disposing fluid through said restricted reservoir opening.

7. The syringe dispensing device defined in claim 6, characterized in that said opposed ends of said collar strap each include an enlarged tab portion which is releasably receivable in a slot in said fixed handle, releasably retaining said fixed handle on said syringe reservoir and aligning said ratchet mechanism relative to said plunger.

8. The syringe dispensing apparatus defined in claim 6, characterized in that said detent is V-shaped and includes an integral transverse release lever extending from adjacent the pivotal support of said detent, said release lever rotating said detent about said pivotal support to release the edge in engagement with said plunger vane and dig the opposed detent edge into said plunger for telescoping said plunger into or out of said syringe reservoir.

9. The syringe dispensing apparatus defined in claim 6, characterized in that said plunger is generally cruciform in cross-section, including four radially extending vanes, said collar alignment means comprising a flange extending transversely from the midportion of said strap portion, said flange having a slot receiving one of said syringe plunger vanes, said fixed handle attached to said opposed free ends of said strap, opposite the slot of said flange, thereby aligning the opposed vane of said syringe plunger with said ratchet mechanism detent for gripping engagement therewith.

* * * * *